US008906883B2

(12) United States Patent
Adolfsson et al.

(10) Patent No.: US 8,906,883 B2
(45) Date of Patent: Dec. 9, 2014

(54) TREATMENT OF ORAL MUCOSITIS BY ADMINISTERING AN IONIC COMPLEX OF CHITOSAN AND A NEGATIVELY CHARGED POLYSACCHARIDE SELECTED FROM HEPARIN, HEPARAN SULFATE AND DEXTRAN SULFATE

(75) Inventors: Lars Adolfsson, Uppsala (SE); Olle Larm, Bromma (SE); Anders Westermark, Mariehamm Aland (FI)

(73) Assignee: Exthera AB, Stockholm (SE)

( * ) Notice: Subject to any disclaimer, the term of this patent is extended or adjusted under 35 U.S.C. 154(b) by 0 days.

(21) Appl. No.: 13/376,947

(22) PCT Filed: Jun. 10, 2010

(86) PCT No.: PCT/SE2010/050650
§ 371 (c)(1),
(2), (4) Date: Dec. 8, 2011

(87) PCT Pub. No.: WO2010/144044
PCT Pub. Date: Dec. 16, 2010

(65) Prior Publication Data
US 2012/0077773 A1   Mar. 29, 2012

(30) Foreign Application Priority Data
Jun. 10, 2009  (SE) ....................................... 0950441

(51) Int. Cl.
| *A61K 31/722* | (2006.01) |
| *A61K 31/721* | (2006.01) |
| *A61K 31/727* | (2006.01) |
| *A61K 31/737* | (2006.01) |
| *A61K 9/10* | (2006.01) |
| *A61K 9/00* | (2006.01) |
| A61K 47/36 | (2006.01) |

(52) U.S. Cl.
CPC .............. *A61K 31/722* (2013.01); *A61K 31/721* (2013.01); *A61K 47/36* (2013.01); *A61K 31/737* (2013.01); *A61K 9/10* (2013.01); *A61K 31/727* (2013.01); *A61K 9/006* (2013.01)
USPC ........................................................ 514/56

(58) Field of Classification Search
None
See application file for complete search history.

(56) References Cited

U.S. PATENT DOCUMENTS

| 6,207,653 | B1 * | 3/2001 | Larm et al. ....................... 514/55 |
| 7,547,433 | B2 * | 6/2009 | Jacob et al. ....................... 424/49 |
| 2004/0167099 | A1 * | 8/2004 | Lawter ............................. 514/55 |
| 2006/0058390 | A1 * | 3/2006 | Sunkara ......................... 514/562 |
| 2008/0299050 | A1 | 12/2008 | Bortz et al. |

FOREIGN PATENT DOCUMENTS

| JP | 2004-525980 A | 8/2004 |
| WO | 9602258 | 2/1996 |
| WO | 9805341 | 2/1998 |
| WO | 02064113 A1 | 8/2002 |
| WO | 02085385 A2 | 10/2002 |
| WO | 03090763 A1 | 11/2003 |
| WO | 2006078211 A1 | 7/2006 |
| WO | 2007135166 A1 | 11/2007 |

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002.*
Nicolatou-Galitis et al. Herpes simplex virus-1 (HSV-1) infection in radiation-induced oral mucositis. Support Care Cancer (2006) 14: 753-762.*
Rubenstein et al. Clinical Practice Guidelines for the Prevention and Treatment of Cancer Therapy—Induced Oral and Gastrointestinal Mucositis. CANCER Supplement May 1, 2004, vol. 100 ,No. 9, pp. 2026-2046.*
International Search Report for PCT/SE2010/050650, Completed by the Swedish Patent Office on Sep. 9, 2010, 4 Pages.
Extended European Search Report for EP 10786461.3, Dated Aug. 14, 2013, 7 Pages.
Knapczyk., International Journal of Pharmaceutics 1993, vol. 93, p. 233-237, "Chitosan hydrogel as a base for semisolid drug forms."
Aksungur et al. Journal of Controlled Release 2004, vol. 98, p. 269-279, "Chitosan delivery system for the treatment of oral mucositis: in vitro and in vivo studies."
English Translation of Russian Office for Russian Application No. 2011152518/15(078860), Dated Jan. 24, 2014, 4 Pages.

* cited by examiner

*Primary Examiner* — Eric Olson
*Assistant Examiner* — Dale R Miller
(74) *Attorney, Agent, or Firm* — Brooks Kushman, P.C.

(57) ABSTRACT

A composition having an ionic complex of chitosan and a negatively charged polysaccharide, selected from the group consisting of heparin, heparan sulfate and dextran sulfate, for use in the treatment of mucositis in a mammalian subject, to a method of preventing or treating mucositis in a mammalian subject, by applying topically a composition having an ionic complex of chitosan and a negatively charged polysaccharide, selected from the group consisting of heparin, heparan sulfate and dextran sulfate. The composition further relates to a pharmaceutical composition for topical administration of an ionic complex of chitosan and heparin.

17 Claims, No Drawings

TREATMENT OF ORAL MUCOSITIS BY ADMINISTERING AN IONIC COMPLEX OF CHITOSAN AND A NEGATIVELY CHARGED POLYSACCHARIDE SELECTED FROM HEPARIN, HEPARAN SULFATE AND DEXTRAN SULFATE

CROSS-REFERENCE TO RELATED APPLICATION

This application is the U.S. national phase of PCT Appln. No. PCT/SE2010/050650 filed Jun. 10, 2010, which claims priority to Swedish application 0950441-6 filed Jun. 10, 2009, the disclosures of which are incorporated in their entirety by reference herein.

FIELD OF THE INVENTION

The present invention relates to a pharmaceutical composition for use in the treatment or prophylaxis of mucositis. The present invention further involves a method of treating or preventing mucositis.

BACKGROUND

Mucositis is the medical term for the painful inflammation and ulceration of the mucous membranes lining the digestive tract. Mucositis often appears as an adverse effect of chemotherapy and radiotherapy treatment for cancer. Mucositis can occur anywhere in the body where mucous membranes are present but is most common in the gastrointestinal tract and oral cavity. Oral mucositis refers to the inflammation and ulceration that occurs in the mouth and is a common and often debilitating side-effect of cancer treatment. Oral mucositis is generally graded on a WHO scale ranging from 1 to 4, 4 being the most severe. In grade 3 oral mucositis, the patient is unable to eat solid food, and in grade 4, the patient is unable to consume liquids as well.

Oral and gastrointestinal mucositis can affect up to 100% of patients undergoing high-dose chemotherapy and hematopoietic stem cell transplantation (HSCT), 80% of patients with malignancies of the head and neck receiving radiotherapy, and a wide range of patients receiving chemotherapy. Alimentary tract mucositis increases mortality and morbidity and contributes to rising health care costs.

For most cancer treatment, about 5-15% of patients get mucositis. However, with 5-fluorouracil (5-FU), up to 40% get mucositis, and 10-15% get grade 3-4 oral mucositis. Irinotecan is associated with severe GI mucositis in over 20% of patients. 75-85% of bone marrow transplantation recipients experience mucositis, of which oral mucositis is the most common and most debilitating, especially when melphalan is used.

Radiotherapy to the head and neck or to the pelvis or abdomen is associated with Grade 3 and Grade 4 oral or GI mucositis, respectively, often exceeding 50% of patients. Among patients undergoing head and neck radiotherapy, pain and decreased oral function may persist long after the conclusion of therapy. Fractionated radiation dosage increases the risk of mucositis to more than 70% of patients in most trials. Oral mucositis is particularly profound and prolonged among HSCT recipients who receive total-body irradiation.

Present treatment of mucositis is mainly supportive. Oral hygiene is the mainstay of treatment; patients are encouraged to clean their mouth every four hours and at bedtime, more often if the mucositis becomes worse. Water-soluble jellies can be used to lubricate the mouth. Salt mouthwash can soothe the pain and keep food particles clear so as to avoid infection. Medicinal mouthwashes may be used such as Chlorhexidine gluconate and viscous Lidocain for relief of pain. Palifermin is a human KGF (keratinocyte growth factor) that has shown to enhance epithelial cell proliferation, differentiation, and migration. Experimental therapies have been reported, including the use of cytokines and other modifiers of inflammation (e.g. IL-1, IL-11 and TGF-beta3), amino acid supplementation (e.g. glutamine), vitamins, colony-stimulating factors, cryotherapy, and laser therapy. Symptomatic relief of the pain of oral mucositis may be provided by barrier protection agents such as concentrated oral gel products (e.g. GELCLAIR™). CAPHOSOL™ is a mouth rinse which has been shown to prevent and treat oral mucositis caused by radiation and high dose chemotherapy. A problem with many of the barrier protection agents is that very frequent application may be required, often as many as 4-10 times per day.

Sores or ulcerations can become infected by virus, bacteria or fungus. Pain and loss of taste perception makes it more difficult to eat, which leads to weight loss. Ulcers may act as a site for local infection and a portal of entry for oral flora that, in some instances, may cause septicemia (especially in immunosuppressed patients). Approximately half of all patients who receive chemotherapy develop such severe oral mucositis that becomes dose-limiting such that the patient's cancer treatment must be modified, compromising the prognosis." Thus, there is still a pressing need for improved methods for preventing and treating mucositis.

DESCRIPTION OF THE INVENTION

It is an object of the present invention to provide a topical pharmaceutical composition which, when administered to a patient suffering from mucositis relieves the symptoms of the mucositis.

Another object of the present invention is to provide a topical pharmaceutical composition which, when administered to a patient suffering from or at risk of developing mucositis, prevents exacerbation or development of the mucositis.

A further object of the present invention is to provide a topical pharmaceutical composition for treatment or prophylaxis of mucositis, which provides a sustained effect, thus reducing the required frequency of administration.

Yet another object of the present invention is to provide a topical pharmaceutical composition for prophylaxis of mucositis, which enables the use of higher dosages of chemotherapy, radiotherapy and/or stem cell therapy in the treatment of cancer in a patient, without causing more suffering for the patient.

The above mentioned objects, as well as further objects which will become apparent to a person skilled in the art in view of the present disclosure, are achieved by the various aspects of the present invention.

In a first aspect thereof, the present invention provides a composition comprising an ionic complex of chitosan and a negatively charged polysaccharide, selected from the group consisting of heparin, heparan sulfate and dextran sulfate, for use in the treatment of mucositis in a mammalian subject.

When solutions of negatively charged polysaccharide and chitosan are mixed, an ionic complex is immediately formed and precipitates. In such a complex, chitosan protects the negatively charged polysaccharide from enzymatic degradation in vivo, and that the half-life and beneficial effect of the negatively charged polysaccharide is thereby considerably prolonged.

The compositions, methods and uses for treatment of mucositis disclosed herein are applicable to mammalian subjects in general and to human subjects in particular.

The composition of the invention may preferably be applied topically to a site in need of treatment, such as for example to a surface of a mucous membrane which has been damaged due to mucositis, or which is at risk of becoming damaged due to mucositis.

When applied to the surface of mucous membranes, such as the mucous membranes of the oral cavity, or wounds, sores or ulcers on mucous membranes, the composition forms a physical barrier covering the surface onto which it is applied. The physical barrier, also referred to as a film, helps to prevent direct contact of the surface with objects or materials that would otherwise be brought into direct contact with potentially exposed nerve endings at the surface, thereby causing discomfort or pain to the patient. Examples of such objects or materials may include, in the case of oral mucositis, the teeth of the patient or foreign materials or substances, such as foodstuff or particles of food, beverages and other foreign objects or substances that may be introduced into the mouth of the patient.

The physical barrier, further helps prevent the introduction of bacteria into wounds, sores or ulcers on mucous membranes, thereby reducing the risk of infection.

Preventing contact of the surface of a wounded mucous membrane with objects or materials that would otherwise be brought into direct contact may further help accelerate the healing process since irritation and infection of the wound can be avoided.

The composition does not merely act as a physical barrier which protects wounded or sensitized mucous membranes. The ionic complex between chitosan and a negatively charged polysaccharide, when applied to a mucous membrane, further provides a slow release of the negatively charged polysaccharide, e.g. heparin, to the membrane. The negatively charged polysaccharide present in the ionic complex is gradually released when the chitosan degrades. Heparin has inherent antimicrobial, anti-inflammatory, pain relieving and wound healing properties. A slow release of heparin at the surface of a wounded mucous membrane is thus highly beneficial to a patient suffering from mucositis.

The composition may be used in the treatment of patients suffering from developed mucositis, e.g. oral mucositis of WHO grade 1, 2, 3 or 4.

The composition may also advantageously be used for prophylactic treatment of a patient at risk of developing mucositis.

Chitosan is a positively charged linear 1,4-bound polysaccharide based on β-D-glucosamine residues. Chitosan is formed by partial N-deacetylation of chitin, a polymer comprised, e.g., in crab and shrimp shells. N-deacetylation may for example be performed by treatment of the chitin with a strong base or acid and results in the conversion of acetamido groups to amine groups. In vivo, chitosan is degraded by lysozyme and other glycosaminodases to mono- and oligomers. Chitosan which is rich in N-acetyl-D-glucosamine is degraded faster in vitro, and probably also in vivo, than a chitosan with a high proportion of D-glucosamine residues. The chitosan used with the composition of the invention may generally have a degree of deacetylation in the range of 50 to 99%. It has been found, however, that a chitosan having a degree of deacetylation in the range of about 80 to 95% is especially useful in a composition for treatment of mucositis. Thus, in an embodiment, the chitosan used in the composition has a degree of deacetylation in the range of 50 to 99%, preferably in the range of 80 to 95%.

Chitosan, degrades under physiological conditions, such as the conditions that may be present in the oral cavity or in the gastrointestinal tract, to physiologically acceptable, non-harmful and readily metabolized sub-components. Most negatively charged polysaccharides also degrade under physiological conditions, such as the conditions that may be present in the oral cavity or in the gastrointestinal tract to non-harmful and readily metabolized sub-components, such as carbohydrate mono- and oligomers. Examples of negatively charged polysaccharides that degrade in vivo to naturally occurring sub-components include heparin, heparan sulfate and dextran sulfate. The composition may preferably comprise chitosan and a negatively charged polysaccharide selected from the group consisting of heparin, heparan sulfate and dextran sulfate. Such a composition is advantageous in that it may be biologically degradable and form non-toxic, naturally occurring and/or readily metabolized residues upon degradation.

In an embodiment, the negatively charged polysaccharide is heparin. Thus, in this embodiment, the inventive composition consists of a chitosan-heparin ionic complex. In such an ionic complex, the weight ratio of chitosan to heparin may be from about 1:1 to 10:1, such as from about 1:1 to about 5:1. Examples of more specific intervals are from about 3:1 to about 4:1, and from about 2:1 to about 3:1. The weight ratio of chitosan to heparin in the ionic complex affects the physical characteristics of the complex, in particular its rheological properties and adhesiveness. Furthermore, having an excess of heparin would entail a risk of unwanted blood-anticoagulation, due to the interaction between heparin and plasma proteins in blood. The ranges given above are to be seen as guidelines for the skilled person to find the optimal ratio based on the particular situation in which the composition is to be used.

In a preferred embodiment of the composition according to this aspect of the invention, the number of positive charges contributed by said chitosan are in excess over the number of negative charges contributed by said negatively charged polysaccharide in the ionic complex. Upon administration of this embodiment of the inventive composition, with an excess of chitosan in comparison to negatively charged polysaccharide on a charge basis, the composition is immobilized at the site of treatment. This is because in general, the surfaces of mucous membranes, and wounds, sores or ulcers on mucous membranes, are negatively charged. The immobilization of the composition in the area to be treated results in a gradual and local release of the negatively charged polysaccharide as the chitosan is degraded.

In an embodiment of the composition, the charge ratio of positive charges in said chitosan to negative charges in said negatively charged polysaccharide is in the range of from 10:1 to 10:8, preferably in the range of from 10:3 to 10:6, more preferably in the range of from 10:4 to 10:5. A charge ratio in the range of from 10:4 to 10:5 is especially advantageous, since it provides very good adhesion to the surface of mucous membranes and wounds, sores or ulcers on mucous membranes caused by mucositis, while still providing a therapeutically relevant release rate of the negatively charged polymer, e.g. heparin, to the surface.

The composition may preferably be formulated for topical administration. More preferably, the composition may be formulated for topical administration to the surface of mucous membranes. In an embodiment, the composition is applied in the form of a mouthwash.

The composition may be in the form of a suspension of particles of the complex of chitosan and heparin in a liquid medium. The liquid medium may preferably be water or water based. Depending on the concentration of the complex in the composition, the composition may be referred to as a suspension or a gel.

The total concentration of the complex of chitosan and said negatively charged polysaccharide in said composition may preferably be selected such that a film of the complex is formed when the composition is applied to a surface.

The viscosity of the composition generally increases with increasing concentration of the complex of chitosan and said negatively charged polysaccharide. The total concentration of the complex of chitosan and said negatively charged polysaccharide in said composition may preferably be selected such that the viscosity of the composition is capable of forming a film on the mucous membranes of the oral cavity of a patient upon rinsing of the patients mouth with the composition.

The total concentration of chitosan and negatively charged polysaccharide in the composition may generally be in the range of from 0.1 to 5%, preferably in the range of from 0.1 to 3% by weight, based on the total weight of the composition. A suitable viscosity may for example be obtained when the total concentration of said chitosan and said negatively charged polysaccharide in the composition is in the range of from 0.5 to 5%, based on the total weight of the composition. A total concentration in the range of from 1 to 3% by weight, based on the total weight of the composition, is preferred.

It has been found that when the composition is provided in the form of a mouthwash, a total concentration of said chitosan and said negatively charged polysaccharide in the composition in the range of from 0.1 to 0.5% by weight, for example in the range of 0.2 to 0.4% by weight, based on the total weight of the composition is useful. Thus, in an embodiment, the total concentration of said chitosan and said negatively charged polysaccharide in the composition is in the range of from 0.1 to 0.5% by weight, based on the total weight of the composition, for example in the range of 0.2 to 0.4% by weight, based on the total weight of the composition.

The composition may further comprise various pharmaceutically acceptable excipients and additives. Examples of such excipients and additives include, but are not limited to buffers, surfactants, viscosity adjusting agents, flavoring agents, and antimicrobial agents, such as anti-fungal agents and anti-bacterial agents. The composition may also comprise an antifoaming agent.

In an embodiment, the composition further comprises an antimicrobial agent, such as an antifungal agent or an antibacterial agent. Examples of such agents include, but are not limited to, methyl paraben and propyl paraben.

In an embodiment, the composition further comprises an antifoaming agent, for example a silicone based antifoaming agent. An antifoaming agent is useful to prevent foaming of the composition when applied, for example, in the form of a mouthwash.

The composition may also comprise additional pharmaceutically active agents, that may further improve the healing or pain relieving effects of the composition. Examples of such additional pharmaceutically active agents include, but are not limited to, analgesic agents, anti-inflammatory agents and antibiotics.

The composition may be useful in the treatment of all types of mucositis, e.g. mucositis affecting the oral cavity, esophageal tract, gastrointestinal tract, genitourinary tracts, and the nasal and respiratory tracts, but is particularly suitable for treatment of oral and gastrointestinal mucositis, especially oral mucositis. The combination of the ability to form a physical barrier covering the surface to be protected and/or treated, and the wound healing properties of the composition, makes it well suited for treatment of oral and gastrointestinal mucositis, such as esophageal mucositis.

Thus, in an embodiment, the mucositis to be treated is oral or gastrointestinal mucositis, and preferably oral mucositis.

The most common cause of mucositis is the treatment of cancer by radiotherapy, chemotherapy or stem cell therapy. The composition is especially useful for treatment of this group patients, since the onset of mucositis may be relatively accurately predicted in relation to the commencement of a radiotherapy, chemotherapy or stem cell therapy procedure. The possibility of predicting the onset of mucositis allows prophylactic treatment of patients at risk of developing mucositis, thereby allowing treatment of the patient even before any symptoms are experienced. Thus, the composition may significantly reduce the pain and discomfort of patients receiving radiotherapy, chemotherapy or stem cell therapy. Furthermore, treatment with the composition, and especially prophylactic treatment, may enable the use of higher dosages of chemotherapy, radiotherapy and/or stem cell therapy in the treatment of cancer in a patient, without causing more suffering for the patient.

Thus, in an embodiment, the composition is for use in the treatment of mucositis caused by treatment of cancer. The treatment of cancer may include one or more therapies selected from the group consisting of chemotherapy, radiotherapy or stem cell therapy.

In a second aspect thereof, the present invention provides a method of preventing or treating mucositis in a mammalian subject, by applying topically a composition comprising an ionic complex of chitosan and a negatively charged polysaccharide, selected from the group consisting of heparin, heparan sulfate and dextran sulfate, to a site in need of treatment.

The term "mammalian", as used herein, includes humans unless otherwise specifically stated.

The term "topical", as used herein, generally means the application of a pharmaceutical composition to body surfaces such as the skin or mucous membranes, for example the mouth, throat, eyes, vagina or anus.

The composition is typically applied topically to the site in need of treatment, such as a wounded, damaged or ulcerous mucous membrane, or a membrane at risk of becoming damaged, e.g. because of a cancer treatment procedure. The composition may preferably be applied in an amount sufficient to form a film, which covers the surface to be treated or protected. The composition may be applied once or a suitable number of times during administration, such that a single layer film or a film having more than one layer is formed. A suitable treatment regimen may be determined by a person skilled in the art, depending for example on the grade and severity of the mucositis and on patient specific factors affecting the duration of the film.

The composition may be applied in any form suitable for topical administration, such as a gel, suspension, lotion, cream, ointment, foam or spray. The composition may preferably be applied in the form of a gel or a suspension. In the treatment of oral mucositis, the composition may preferably be applied in the form of a mouthwash.

The composition used in the method of the second aspect of the invention may be further defined as described above in respect of the first aspect of the invention.

The type of mucositis may be further defined as described above in respect of the first aspect of the invention.

The cause of the mucositis may be further defined as described above in respect of the first aspect of the invention.

The method of treatment of mucositis may be especially advantageous when used prophylactically to prevent symptoms of mucositis from developing in a patient at risk of developing mucositis. Thus, in an embodiment of the method, the patient has not yet developed mucositis, but is at risk of developing mucositis. The patient may for example be subject to treatment by chemotherapy, radiotherapy or stem cell therapy, or intended to become subject to such treatment. Treatment with the composition, and especially prophylactic treatment, may significantly reduce the risk of a patient undergoing cancer treatment of developing mucositis which is so severe that it becomes dose limiting. Treatment with the composition, and especially prophylactic treatment, may enable the use of higher dosages of chemotherapy, radiotherapy and/or stem cell therapy in the treatment of cancer in a patient, without causing more suffering for the patient.

In a third aspect thereof, the present invention provides a pharmaceutical composition suitable for topical administration comprising a suspension of chitosan and heparin, wherein said chitosan has a degree of deacetylation in the range of 80 to 95%, the charge ratio of positive charges in said chitosan to negative charges in said negatively charged polysaccharide is in the range of from 10:4 to 10:5, and the total concentration of said chitosan and said negatively charged polysaccharide in said composition is in the range of from 0.1 to 5%, preferably in the range of from 0.1 to 3% by weight, such as from 1 to 3% by weight, based on the total weight of the composition.

It has been found that when the composition is provided in the form of a mouthwash, a total concentration of said chitosan and said negatively charged polysaccharide in the composition in the range of from 0.1 to 0.5% by weight, for example in the range of 0.2 to 0.4% by weight, based on the total weight of the composition is useful. Thus, in an embodiment, the total concentration of said chitosan and said negatively charged polysaccharide in the composition is in the range of from 0.1 to 0.5% by weight, based on the total weight of the composition, for example in the range of 0.2 to 0.4% by weight, based on the total weight of the composition.

The composition of the third aspect of the invention is especially useful in the treatment of mucositis. The present inventors have found that a composition according to the third aspect of the invention provides a very beneficial combination of properties for treatment of wounded, damaged or ulcerous mucous membranes. The beneficial combination of properties includes good wound healing and pain relieving effects, an advantageous degradation time span, optimized adhesion to surfaces of mucous membranes and wounds, sores or ulcers on mucous membranes, and good film forming properties allowing the formation of a physical barrier over a mucous membrane surface.

Providing a composition which is capable of forming a sufficiently durable protective film on mucous membranes, such as those of the oral cavity or throat, is difficult. However, a composition according to the third aspect of the invention surprisingly provides a protective film which is not only sufficiently durable and adhesive, but which also provides a controlled release of heparin to the site under treatment, and which is biologically degraded to physiologically acceptable degradation products. Further embodiments and advantages of the composition of the third aspect of the invention are as described in respect of the first aspect of the invention.

In a fourth aspect thereof, the present invention further provides the use of a composition comprising an ionic complex of chitosan and a negatively charged polysaccharide, selected from the group consisting of heparin, heparan sulfate and dextran sulfate, in the manufacture of a medicament for use in the treatment of mucositis in a mammalian subject. In other words, the present invention further provides a composition comprising an ionic complex of chitosan and a negatively charged polysaccharide for use in the treatment of mucositis in a mammalian subject.

The use according to the fourth aspect of the invention may be further defined as described above in respect of the first aspect of the invention.

All features of all embodiments of all aspects of the invention can be used in any possible combination thereof, provided that such combination is not demonstrably unfeasible as determined without undue experimentation by a person having ordinary skill in the art.

EXAMPLES

For the further understanding of the invention the following non-limiting examples are given:

Example 1

Preparation of a Topical Composition for Treatment of Mucositis

Methylparaben (1.31 g) and propylparaben (0.131 g) were dissolved in 0.115 M acetate buffer (1 L, pH 4.5) during stirring and heating. When the parabens had been completely dissolved, the solution was cooled to room temperature.

To 160 g of the cooled solution saccharin sodium (0.5 g) was added and dissolved under stirring. 2.5 g of chitosan (ChitoClear®, Primex ehf, Norway) with a degree of deacetylation of 90% was then added and the solution was stirred until all of the chitosan had been dissolved.

To another 31 g of the paraben containing acetate buffer solution 1.0 g of heparin sodium (Scientific Protein Laboratories) was added and dissolved during stirring.

The heparin solution and the chitosan solution were combined and the suspension formed was stirred during 5 minutes. 50 g of a sorbitol solution (70% solution in water) were then added to the suspension and the stirring was continued for another 2 minutes. Peppermint oil (0.5 g) was dissolved in polyethylene glycol sorbitan monolaurate (tween 20, 4.5 g) under stirring, and the peppermint solution was added to the heparin/chitosan mixture and stirring was continued for another 5 minutes.

Example 2

Preparation of a Topical Composition for Treatment of Mucositis

Methylparaben (2.53 g) and propylparaben (0.253 g) were dissolved in 0.015 M acetate buffer (1 L, pH 4.5) during stirring and heating. When the parabens had been completely dissolved, the solution was cooled to room temperature.

To 160 g of the cooled solution saccharin sodium (0.2 g) was added and dissolved under stirring. To the solution, 37.5 mg antifoaming agent (Simethicone PD30, Basildon Chemical Company Ltd, England) were added during stirring. 0.625 g of chitosan (ChitoClear®, Primex ehf, Norway) with a degree of deacetylation of 90% was then added and the solution was stirred until all of the chitosan had been dissolved.

To another 38 g of the paraben containing acetate buffer solution 0.25 g of heparin sodium (Scientific Protein Laboratories) was added and dissolved during stirring.

The heparin solution and the chitosan solution were combined and the suspension formed was stirred during 5 minutes. 50 g of a sorbitol solution (70% solution in water) were then added to the suspension and the stirring was continued for another 2 minutes. Peppermint oil (0.2 g) was dissolved in polyethylene glycol sorbitan monolaurate (tween 20, 1.0 g) under stirring, and the peppermint solution was added to the heparin/chitosan mixture and stirring was continued for another 5 minutes.

Example 3

Treatment of a Human Patient Suffering from Mucositis

A male patient, 71 years old, was radiated against a head and neck malignant tumour. Before radiation the patient had undergone regular dental care according to the treatment protocol. Like many others this patient suffered from a radiation induced mucositis. In his case the mucositis was of the most severe degree, with spontaneous ulcerations in the oral cavity. The mucositis made eating and drinking very painful and strongly reduced the quality of life.

The patient was treated with the gel suspension prepared as in Example 1. The suspension was administered by allowing the patient to rinse his mouth with the 5 mL of the suspension and then discharge the residue. The procedure was repeated 3 times, with 5 mL of suspension for each repetition. Administration was repeated once more the same day with another administration of 3×5 mL of the suspension. Already the day after the patient received the two treatments, he felt a relief from his ulcers and pain, and could eat and drink normally. On his own initiative he was even eating crab meat without experiencing mucosal pain.

The invention claimed is:

1. A method of treating oral mucositis in a mammalian subject comprising the steps: applying topically a composition comprising an ionic complex of chitosan and a negatively charged polysaccharide, selected from the group consisting of heparin, heparan sulfate and dextran sulfate, to a site in need of treatment wherein the composition has a charge ratio of positive charges in the chitosan to negative charges in the negatively charged polysaccharide in a range of 10:3 to 10:6.

2. The method according to claim 1, wherein the chitosan has a degree of deacetylation in a range of 50 to 99%.

3. The method according to claim 1, wherein the chitosan has a degree of deacetylation in a range of 80 to 95%.

4. The method according to claim 1, wherein the negatively charged polysaccharide is heparin.

5. The method according to claim 1, wherein the composition has a charge ratio of positive charges in the chitosan to negative charges in the negatively charged polysaccharide in a range of 10:4 to 10:5.

6. The method according to claim 1, wherein the total concentration of the chitosan and the negatively charged polysaccharide in the composition is in a range of 0.1 to 5%, based on a total weight of the composition.

7. The method according to claim 1, wherein the total concentration of the chitosan and the negatively charged polysaccharide in the composition is in a range of 0.1 to 3% by weight, based on a total weight of the composition.

8. The method according to claim 1, wherein the total concentration of the chitosan and the negatively charged polysaccharide in the composition is in a range of 0.5 to 5%, based on a total weight of the composition.

9. The method according to claim 1, wherein the total concentration of the chitosan and the negatively charged polysaccharide in the composition is in a range of 1 to 3% by weight, based on a total weight of the composition.

10. The method according to claim 1, wherein the composition further comprising an antimicrobial agent.

11. The method according to claim 10, where the antimicrobial agent is methyl paraben and/or propyl paraben.

12. The method according to claim 1, wherein the composition further comprising an antifoaming agent.

13. The method according to claim 1, wherein the oral mucositis is caused by treatment of cancer, chemotherapy, radiotherapy and/or stem cell therapy.

14. The method according to claim 1, wherein the composition is applied in a form of a mouthwash.

15. The method according to claim 1, wherein applying topically includes body surfaces selected from the group consisting of mouth and throat.

16. The method according to claim 1, wherein the composition further comprising buffer, surfactant, viscosity adjusting agent, flavoring agent, antimicrobial agent and antifoaming agent.

17. A method of treating oral mucositis in a mammalian subject comprising the steps: applying topically a composition comprising an antimicrobial agent, an antifoaming agent, an ionic complex of chitosan and a negatively charged polysaccharide of heparin, the chitosan has a degree of deacetylation in a range of 80 to 95%, the composition has a charge ratio of positive charges in the chitosan to negative charges in the heparin in a range of 10:4 to 10:5, the composition having a total concentration of the chitosan and the heparin in a range of 0.1 to 3% by weight, to a body surface in need of treatment, wherein the body surface is selected from the group consisting of mouth and throat.

* * * * *